(12) United States Patent
Moruzzi et al.

(10) Patent No.: US 10,579,035 B2
(45) Date of Patent: Mar. 3, 2020

(54) QUALITY MONITORING IN A PACKAGING LINE

(71) Applicant: TETRA LAVAL HOLDINGS & FINANCE S.A., Pully (CH)

(72) Inventors: Guido Moruzzi, S. Lazzaro di Savena (IT); Gianni Corazzari, Cavezzo (IT); Davide Trombini, Sjöbo (SE); Marco Hugo Gutiérrez, Madrid (ES)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 354 days.

(21) Appl. No.: 15/517,715

(22) PCT Filed: Oct. 6, 2015

(86) PCT No.: PCT/EP2015/073037
§ 371 (c)(1),
(2) Date: Apr. 7, 2017

(87) PCT Pub. No.: WO2016/055470
PCT Pub. Date: Apr. 14, 2016

(65) Prior Publication Data
US 2017/0329298 A1    Nov. 16, 2017

(30) Foreign Application Priority Data
Oct. 9, 2014 (SE) ...................... 1451204

(51) Int. Cl.
*G05B 19/048* (2006.01)
*G01N 33/00* (2006.01)
(Continued)

(52) U.S. Cl.
CPC ........... *G05B 19/048* (2013.01); *G01N 33/00* (2013.01); *G06Q 10/06* (2013.01); *G06Q 30/018* (2013.01);
(Continued)

(58) Field of Classification Search
CPC ........... G01N 2033/0081; G01N 33/00; G05B 19/048; G05B 2219/23101; B65B 17/00;
(Continued)

(56) References Cited

U.S. PATENT DOCUMENTS

| 4,307,555 A | 12/1981 | Mlodozeniec et al. |
| 5,305,887 A * | 4/1994 | Krieg .................... B07C 5/3408 209/3.1 |

(Continued)

FOREIGN PATENT DOCUMENTS

| EP | 0 086 059 A2 | 8/1983 |
| EP | 0 222 935 A1 | 5/1987 |

(Continued)

OTHER PUBLICATIONS

International Search Report (PCT/ISA/210) dated Dec. 11, 2015, by the European Patent Office as the International Searching Authority for International Application No. PCT/EP2015/073037.

(Continued)

*Primary Examiner* — Andrew M Tecco
*Assistant Examiner* — Nicholas E Igbokwe
(74) *Attorney, Agent, or Firm* — Buchanan Ingersoll & Rooney PC

(57) ABSTRACT

Information is obtained from a package filling machine, regarding sampling occasions in the form of sampling records. Each sampling record comprises a first time stamp for the sampling occasion, information describing a trigger for the sampling occasion, a number of package samples taken at the sampling occasion, and a second time stamp that specifies when the package samples were taken. Analysis information regarding contaminated package samples is obtained from a package sample analysis system. The sampling records and analysis information are processed to link contaminated package samples with sampling occasions. A (Continued)

table is generated that comprises, for each sampling occasion, the first time stamp, the information that describes a trigger for the sampling occasion, the number of package samples taken at the sampling occasion, the second time stamp and a number of contaminated package samples at the sampling occasion.

8 Claims, 5 Drawing Sheets

(51) Int. Cl.
    *G06Q 30/00*     (2012.01)
    *G06Q 10/06*     (2012.01)

(52) U.S. Cl.
    CPC ............... *G01N 2033/0081* (2013.01); *G05B 2219/23101* (2013.01)

(58) Field of Classification Search
    CPC ......... B65B 61/26; B65B 57/02; B65B 53/00; G06Q 30/018; Y04S 10/54
    See application file for complete search history.

(56) References Cited

U.S. PATENT DOCUMENTS

| | | | | |
|---|---|---|---|---|
| 5,314,072 A * | 5/1994 | Frankel | ................ | B07C 5/3408 |
| | | | | 209/44.1 |
| 5,523,560 A * | 6/1996 | Manique | ............ | G01N 21/9027 |
| | | | | 209/526 |
| 5,569,606 A * | 10/1996 | Fine | .................... | G01N 1/2226 |
| | | | | 436/43 |
| 2004/0085561 A1* | 5/2004 | Fromherz | .............. | G06Q 10/06 |
| | | | | 358/1.13 |
| 2006/0149407 A1* | 7/2006 | Markham | .............. | B23Q 35/12 |
| | | | | 700/108 |
| 2006/0259182 A1* | 11/2006 | Mantell | ................. | B65B 61/025 |
| | | | | 700/213 |
| 2009/0271243 A1* | 10/2009 | Sholl | .................... | G06Q 30/018 |
| | | | | 434/365 |
| 2010/0175352 A1 | 7/2010 | Soloman | | |
| 2012/0173447 A1* | 7/2012 | Ljungkrantz | .......... | G06Q 10/08 |
| | | | | 705/333 |
| 2013/0232924 A1* | 9/2013 | Bergman | .......... | G05B 19/4183 |
| | | | | 53/507 |

FOREIGN PATENT DOCUMENTS

| | | |
|---|---|---|
| WO | WO 2005/103984 A2 | 11/2005 |
| WO | WO 2012/089447 A1 | 7/2012 |

OTHER PUBLICATIONS

Written Opinion (PCT/ISA/237) dated Dec. 11, 2015, by the European Patent Office as the International Searching Authority for International Application No. PCT/EP2015/073037.

International-Type Search Report (ITS 201) dated May 6, 2015, by the Swedish Patent Office in counterpart Swedish Application No. 1451204-0.

Felton, 'Remington Essentials of Pharmaceutics', Pharmaceutical Press, 2012 (month unknown), pp. 163-165.

* cited by examiner

| SAMPLING OCCASION TIME STAMP₁ | TRIGGER INFORMATION₁ | NUMBER OF SAMPLES TAKEN₁ | ACTUAL SAMPLING TIME STAMP₁ |
|---|---|---|---|
| SAMPLING OCCASION TIME STAMP₂ | TRIGGER INFORMATION₂ | NUMBER OF SAMPLES TAKEN₂ | ACTUAL SAMPLING TIME STAMP₂ |
| ⋮ | | | |
| SAMPLING OCCASION TIME STAMP_N | TRIGGER INFORMATION_N | NUMBER OF SAMPLES TAKEN_N | ACTUAL SAMPLING TIME STAMP_N |

*Fig. 2*

| SAMPLING OCCASION TIME STAMP₁ | TRIGGER INFORMATION₁ | NUMBER OF SAMPLES TAKEN₁ | ACTUAL SAMPLING TIME STAMP₁ | NUMBER OF CONTAMINATED SAMPLES₁ |
|---|---|---|---|---|
| SAMPLING OCCASION TIME STAMP₂ | TRIGGER INFORMATION₂ | NUMBER OF SAMPLES TAKEN₂ | ACTUAL SAMPLING TIME STAMP₂ | NUMBER OF CONTAMINATED SAMPLES₂ |
| ⋮ | | | | |
| SAMPLING OCCASION TIME STAMP_N | TRIGGER INFORMATION_N | NUMBER OF SAMPLES TAKEN_N | ACTUAL SAMPLING TIME STAMP_N | NUMBER OF CONTAMINATED SAMPLES_N |

| ACTUAL SAMPLING TIME STAMP$_1$ | NUMBER OF CONTAMINATED SAMPLES$_1$ | CONTAMINATION DETAILS$_1$ |
|---|---|---|
| ACTUAL SAMPLING TIME STAMP$_2$ | NUMBER OF CONTAMINATED SAMPLES$_2$ | CONTAMINATION DETAILS$_2$ |
| ⋮ | | |
| ACTUAL SAMPLING TIME STAMP$_N$ | NUMBER OF CONTAMINATED SAMPLES$_N$ | CONTAMINATION DETAILS$_N$ |

| AUXILIARY INFORMATION$_1$ |
|---|
| AUXILIARY INFORMATION$_2$ |
| ⋮ |
| AUXILIARY INFORMATION$_N$ |

QUALITY MONITORING IN A PACKAGING LINE

TECHNICAL FIELD

Embodiments herein relate to methods and arrangements in a packaging line monitoring system, PLMS, where information related to package samples are processed.

BACKGROUND

In a typical packaging line, comprising a filling machine, where packages are filled with foodstuff or other content that is associated with very low tolerance regarding, e.g., bacteria content, a schedule or plan should exist according to which an operator takes package samples from the packaging line for incubation and sterility analysis. During such analysis the vast majority of the samples are typically found sterile. Nevertheless, when an unsterile sample is found during such sampling and analysis, this triggers some kind of action. Such actions may be an inspection of a warehouse in which the packages from the packaging line have been stored and subsequent re-sampling of the stored packages.

Typically, a sampling plan specifies obtaining a few samples at regular time intervals, this is a so called "random sampling". Samples may also be obtained every time a steady state of a filling machine is disturbed, this is a so called "aimed sampling" or "sampling at events". Typical events that trigger such aimed sampling may be production start or re-start after a stop, splicing of materials making up the packages, change of filling product, and many others depending on, e.g., previous history of the machinery in the packaging line and depending on the requirements of the specific user of the packaging line.

Furthermore, a typical sampling plan may involve sampling and analyzing the samples in a destructive way from 1 up to 10 samples per 1000 produced packages. This may mean obtaining some 100 to 1000 packages per packaging line per day, assuming a daily production rate of 100 000 packages. An ordinary overall defect (e.g. in the form of bacterial contamination) rate, unless an extraordinary event or "crisis" occurs, is well below 1 defect sample in 1000 samples. In other words, a normal occurrence of defects in the samples does not exceed a few units per packaging line per month.

Very often no record is kept of the large amount of sampled packages that are found to be sterile, and only the very few non-sterile packages are recorded. This is explainable by understanding the large administrative effort that would be needed to register and classify hundreds of packages sampled per filling machine per day, which are generally sterile, with the exception of a very few contaminated packages that are found maybe once per week.

However, in this situation a lot of information is lost, and specifically the "denominator" of the definition of aseptic performance is missing or loosely defined. In particular, it is difficult to identify specific situations (periods, lines, organization set-ups, operational modes etc.) which may potentially be connected with higher or lower aseptic performance; thus potential causes for particularly bad (or good) aseptic performance are difficult to identify and the effectiveness of possible corrective actions cannot be verified on objective basis. Moreover, typically not much effort is spent in studying quality trends, or it is done but on the basis of uncertain or unreliable data. Prior art systems and methods are thus incapable of making use of the mass of accumulated data in order to maintain or improve the quality level of the output from the packaging line.

SUMMARY

In order to mitigate at least some of the drawbacks as discussed above, there is provided in a first aspect of embodiments herein a method in a packaging line monitoring system. The method comprises obtaining, from a package filling machine, information regarding sampling occasions in the form of a plurality of sampling records. Each sampling record comprises a first time stamp for the sampling occasion, information that describes a trigger for the sampling occasion, a number of package samples taken at the sampling occasion, and a second time stamp that specifies when the package samples were taken. Analysis information regarding contaminated package samples is then obtained from a package sample analysis system and the sampling records and the analysis information are processed, whereby information is obtained that links contaminated package samples with sampling occasions. A table is generated that comprises, for each sampling occasion, the first time stamp for the sampling occasion, the information that describes a trigger for the sampling occasion, the number of package samples taken at the sampling occasion, the second time stamp that specifies when the package samples were taken, and a number of contaminated package samples at the sampling occasion.

In some embodiments, the analysis information regarding a contaminated package sample may comprise information that represents a point in time at which the package sample was filled in the filling machine. The processing of the sampling records and the analysis information then comprises a comparison between the information that represents a point in time at which the package sample was filled and any of the first time stamp and the second time stamp.

The information that describes a trigger for the sampling occasion may in some embodiments comprise information about an event in the package filling machine.

In other embodiments, the information that describes a trigger for the sampling occasion may comprise information that specifies that the sampling occasion has been chosen randomly or pseudo-randomly.

In some embodiments, the analysis information regarding a contaminated package sample may comprise detail information of a contamination classification scheme. In such embodiments, the generation of a table comprises the detail information of the contamination classification scheme.

In some embodiments, the method may comprise obtaining auxiliary information regarding a contaminated package, for example from a location at which packages filled by the filling machine are stored such as a warehouse or a retailer. This auxiliary information may comprise information that represents a point in time at which the contaminated package was filled in the filling machine. In these embodiments, the sampling records and the auxiliary information are processed whereby information is obtained that links the contaminated package with the point in time at which it was filled. The generation of the table may then comprise the information that links the contaminated package with the point in time at which it was filled.

In other words, the embodiments of the present disclosure provide advantages at least in that the typically very large number of samples obtained in packaging line monitoring system, contaminated as well as non-contaminated, are recorded. The analysis system simply provides additional information regarding the (normally few) contaminated samples, as all relevant information is already logged by the filling machine. The embodiments herein links the samples, the good and the bad ones, to the specific moment in which they were produced in the filling machine. The table that is generated is a complete record of the structure of the sampling of packages at a filling machine as well as a detailed record of analytical results; at the same time it is an easily available database that can be used when, e.g., tracing production parameters in a filling machine and how these production parameters have affected the samples taken at the machine.

That is, the embodiments herein enables streamlining and simplifying of the work of sampling, incubation and analysis of package samples, in such a way that it becomes easy to retain detailed data of sampling and sterility analysis, that can be subsequently used. Information about samples taken and found to be OK is provided automatically, thereby limiting manual tasks, (which is typical for prior art systems) to insertion of information on defective units. Samples taken are presumed sterile, and, unless found contaminated, no further information is needed from the analysis system in the laboratory. In this way, for instance, it becomes easy to compare the quality level before and after a certain change of conditions in the filling machine; or periods of particularly good (or bad) quality can be identified and search for root causes triggered. Corrective actions can be verified by direct examination of their effect on the quality level obtained via the samples.

In a second aspect there is provided a packaging line monitoring system apparatus that comprises a processor, a memory and input/output circuitry. The memory contains instructions executable by the processor whereby the processor is operative to control the packaging line monitoring system apparatus by performing the method as summarized above.

In a third aspect there is provided a computer program that comprises instructions which, when executed on at least one processor in a packaging line monitoring system apparatus, cause the packaging line monitoring system apparatus to carry out the method as summarized above.

In a fourth aspect there is provided a carrier comprising the computer program as summarized above, wherein the carrier is one of an electronic signal, an optical signal, a radio signal and a computer readable storage medium.

Embodiments of these second, third and fourth aspects provide technical effects and advantages that correspond to those of the method according to the first aspect.

DETAILED DESCRIPTION

Figure 1:
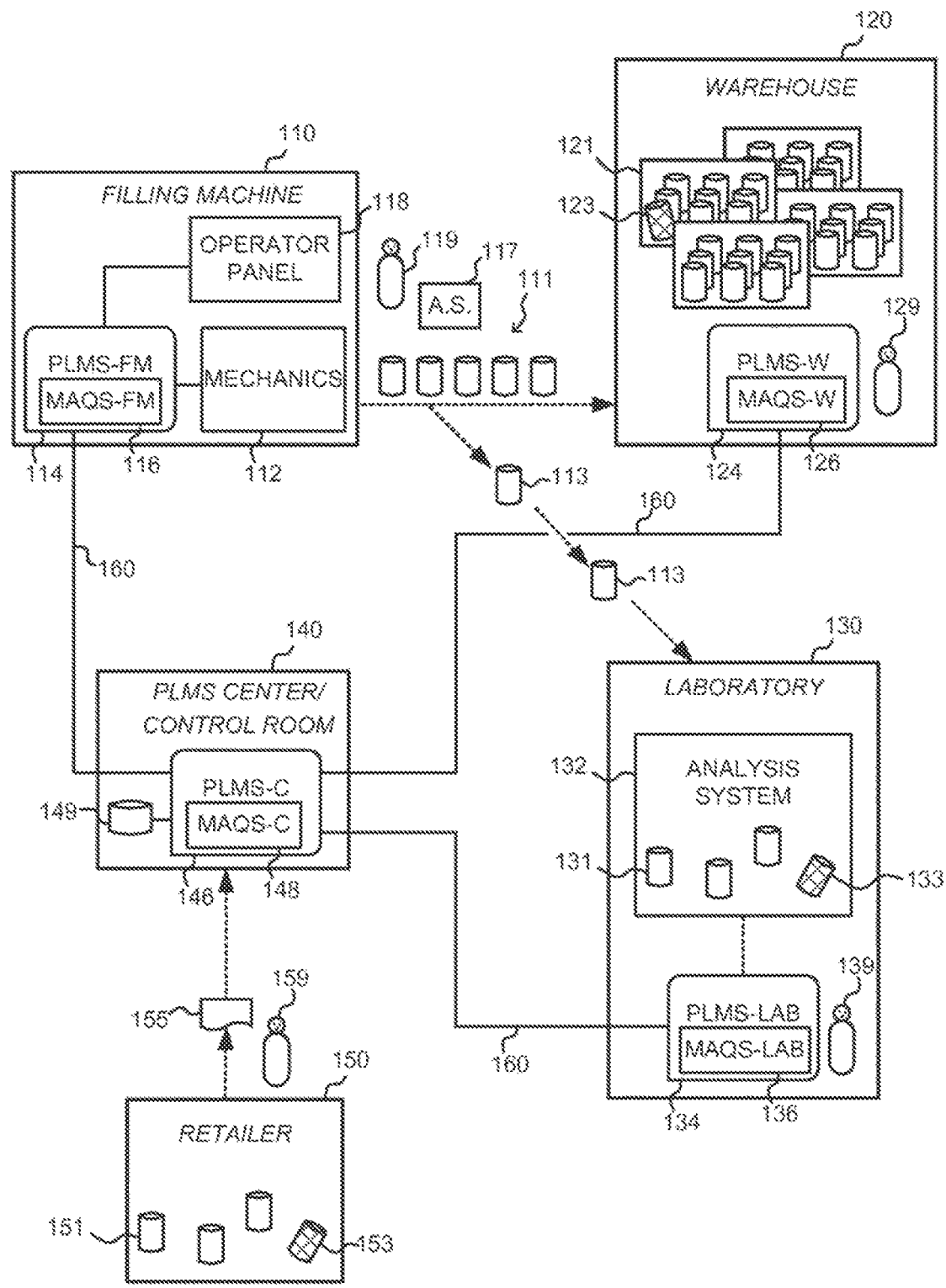
FIG. 1 is a block diagram that schematically illustrates communicating entities that are involved in package handling, FIG. 2 schematically illustrates sampling records, FIG. 3a-c schematically illustrate tables generated in a packaging line monitoring system.

FIG. 1 shows a filling machine, FM, 110 that is configured to output packages 111 that are filled with foodstuff. The FM 110 comprises a large number of components and subsystems. However, not all of these are necessary to illustrate in detail the present disclosure because the skilled person will readily see how to realize the embodiments described herein without such details. The FM 110 comprises mechanics 112, a FM control system 114 and an operator panel 118. The mechanics 112 typically comprises, as the skilled person will realize, package handling and filling means that are suitable for filling packages with foodstuff. The operator panel 118 typically comprises a graphics display and various input means such as soft buttons etc. An operator 119 interacts with the FM 110 via the operator panel 118. The operator 119 may be a human operator, who then interacts via the operator panel 118, but in some embodiments it is foreseen that the operator 119 is a more or less automatic sampling machine that performs the functions of a human operator. Needless to say, in case the operator is an automatic sampling machine, there is no need for interaction via the operator panel 119.

With regard to the FM control system 114, it comprises hardware and software functionality that forms part of a distributed packaging line monitoring system, PLMS, and this part of the PLMS is consequently labeled by the expression PLMS-FM to indicate the modularity of the PLMS. A part of the PLMS-FM 114 is a function block denoted machine aided quality sampling, MAQS-FM, 116. The operator 119 interacts with the PLMS-FM 114 and with the MAQS-FM 116 via the operator panel 118. It is to be noted that the expressions PLMS and MAQS (here and in the description to follow) are used as abbreviations as defined above and no further interpretation of these abbreviations are intended.

An analysis system 117 may also be operated by the operator 118. Such an analysis system 117 may be configured to enable detection whether or not package samples 113 of the packages 111 are contaminated or not. It is to be noted that the analysis system 117 may comprise simple tools as well as measuring means. For example, a more advanced analysis system 117 may comprise means that operate more or less automatically and connects to the PLMS-FM 114. On the other hand, a very simple analysis system 117 may comprise only means that enables the operator 119 to open a package and view it's content and then convey information about such a package sample to the PLMS-FM and the MAQS-FM via the operator panel 118. Analysis performed at the filling machine 110, whether performed by the operator 119 using simple tools or performed by means of any kind of measuring of the packages, may be seen more as a compliance test than a contamination analysis. That is, packages are typically required to fulfil one or more specifications regarding shape, weight, tightness etc. and the analysis at the filling machine 110 may then entail checking whether or not sampled packages fulfil such specifications. Any deviation may than be considered as a sample being non-compliant or having a low quality and the operator may then interact with the operator panel to provide appropriate information to the PLMS-FM 114.

The packages 111 are provided to a warehouse 120 in which the packages are stored as illustrated by package storage units 121. The warehouse 120 comprises PLMS hardware and software functionality that forms part of the undistributed PLMS and this part of the PLMS is consequently labeled by the expression PLMS-W 124. A part of the PLMS-W 124 is a function block denoted MAQS-W 126. A warehouse operator 129 may interact with the PLMS-W 124 and with the MAQS-W 126 via suitable means (not illustrated) such as a display and a keyboard. As will be discussed further below, contaminated packages 123 may be identified, typically by the warehouse operator 129, and reported via the MAQS-W 126.

As will be discussed in more detail below, package samples 113 that are taken from the packages 111 are provided to a laboratory 130. In the laboratory 130, the package samples 113 are subjected to contamination analysis in an analysis system 132 operated by a laboratory operator 139. The analysis system 132 is configured to perform suitable contamination analysis and identify contaminated package samples 133. For example, analysis for sterility may be performed. Such analysis requires the samples to be incubated for some time, typically 2-7 days. Consequently, analysis results are available after some time from the sampling time. In addition to determining sterility of the samples (i.e. "sterile" vs. "contaminated") the laboratory 130 may desire to note other information, such as the method(s) used in the analysis, incubation time and temperature, the results of some assays that may give indications on the contaminating organism(s), and even the exact microbiological identification if available.

In addition to such advanced analysis, a more simple so-called "laboratory check" can be done. Such a check may entail checking for package integrity, similar to the compliance check that the operator 119 at the filling machine 110 may perform. However, such a check at the laboratory 130 is on which involves determinations that cannot be made by the operator 119 because they require some time and reagents that typically are not available to the operator 119 at the filling machine 110.

The laboratory 130 comprises PLMS hardware and software functionality that communicates with the analysis system 132 and forms part of the distributed PLMS and this part of the PLMS is consequently labeled by the expression PLMS-LAB 134. A part of the PLMS-LAB 134 is a function block denoted MAQS-LAB 136. The laboratory operator 139 may interact with the PLMS-LAB 134 and with the MAQS-LAB 136 via suitable means (not illustrated) such as a display and a keyboard. For example, as will be discussed further below, the laboratory operator 139 may provide information about the packages 131 and the contaminated packages 133 via the MAQS-LAB 136.

A retailer 150, such as a supermarket or similar outlet has packages 151 for sale. As will be discussed further below, a retailer operator 159 at the retailer 150 may generate a report 155, via any suitable reporting means, that comprises information about the packages 151 and, specifically, regarding contaminated packages 153 that have been discovered at the retailer 150 (or reported to the retailer 150 from a customer having obtained a package from the retailer 150 and subsequently discovered a defect).

A PLMS Centre 140 may be a part of a control room at a factory site that also comprises the filling machine 110. The PLMS Centre 140 comprises PLMS hardware and software functionality that communicates with corresponding hardware and software functionality in the filling machine 110, the warehouse 120, the laboratory 130 and, via reports 155, also with the retailer 150. However, reports 155 from the retailer 150 are typically conveyed via channels available to the retailer, such as a supplier (not shown in FIG. 1) or the warehouse 120.

The PLMS hardware and software functionality of the PLMS Centre 140 forms part of the distributed PLMS and this part of the PLMS is consequently labeled by the expression PLMS-C 146. A part of the PLMS-C 146 is a function block denoted MAQS-C 148 and a database 149 is connected to the PLMS-C 146 for storage of any information in the context of the present disclosure.

Figure 4A:
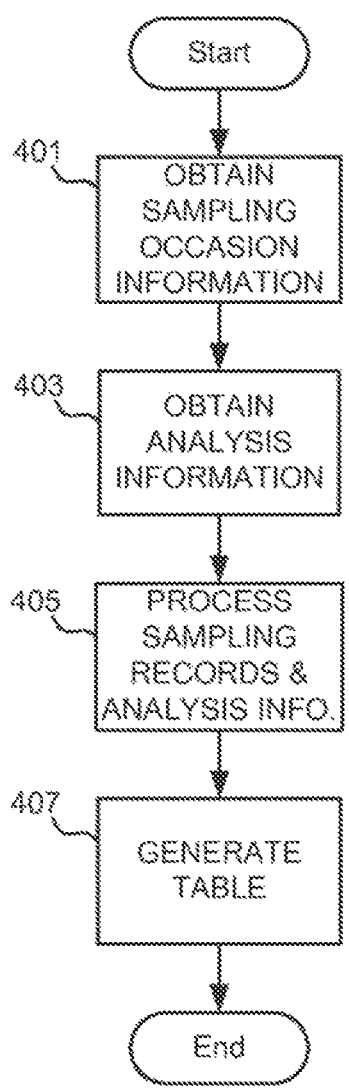
FIGS. 4a-b are flow charts of methods in a packaging line monitoring system.
Figure 4B:
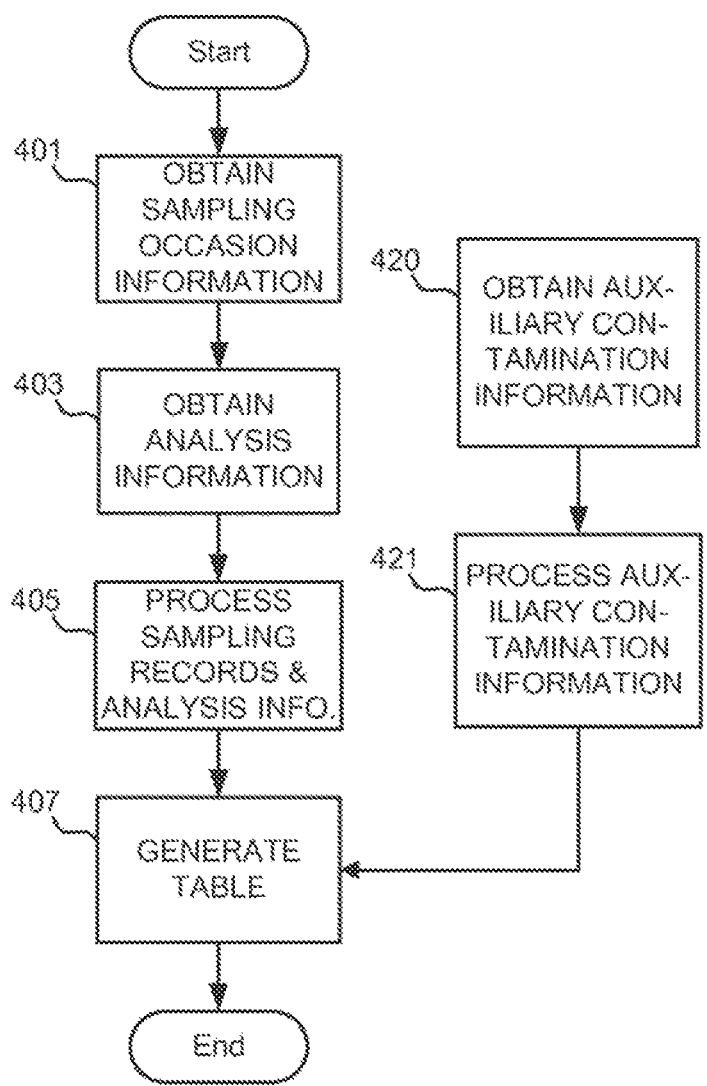

Turning now to FIGS. 2-4, and with continued reference to FIG. 1, embodiments of methods in the PLMS-C 146 will be described in some detail. The method comprises a number of actions that will be described below. The actions of the methods are realized by means of software instructions being executed in a processor in the PLMS-C, which interacts with processors in PLMS-FM 114, PLMS-W 124 and PLMS-LAB 134.

The filling machine 110, i.e. the PLMS-FM, is aware of an already establishing sampling plan. When the conditions for sampling occur, according to the sampling plan, the filling machine 110 calls the operator 119 for doing the actual manual actions that are needed to collect the samples 113 from the packages 111 that are being output from the filling machine 110. When the operator 119 has performed the sampling, he/she sends an acknowledgement to the filling machine 110 via the operator panel 118, which results in a recording in the PLMS-FM 114 of the sampling. Alternatively, if no acknowledgement is received from the operator 119, the PLMS-FM 114 in the filling machine 110 records that the conditions for sampling had occurred, but no sample was actually collected by the operator 119. Both random and aimed sampling can be treated as above. However random sampling can also be left to the initiative of the operator 119, who sends a signal, for example by pressing a button on the operator panel 118, every time a random sample is collected. The PLMS-FM 114 in the filling machine 110 should, ideally, in such a case have knowledge about the number of package samples that should be collected at each random sampling occasion.

Action 401

Information regarding sampling occasions in the form of a plurality of sampling records 201 is obtained from the filling machine 110. As FIG. 2 illustrates, each sampling record 201 comprises a first time stamp 203 for the sampling occasion, information that describes a trigger 205 for the sampling occasion, a number of package samples 207 taken at the sampling occasion, and a second time stamp 209 that specifies when the package samples were taken.

In some embodiments, the information that describes the trigger 205 for the sampling occasion comprises information about an event in the package filling machine 110. Such events may be exemplified by production start, re-start after short or normal stop, longitudinal sealing strip splice, packaging material reel splice, change of filling product, change of filling tank, and end of production etc.

In other embodiments, where the trigger 205 is not associated with an event in the package filling machine 110, the information that describes the trigger 205 for the sampling occasion comprises information that specifies that the sampling occasion has been chosen randomly or pseudo-randomly.

Action 403

Analysis information regarding contaminated package samples 133 is obtained from a package sample analysis system, which may be any of the analysis system 132 in the laboratory 130 and the analysis system 117 operated by the operator 119 at the filling machine 110.

For example, the analysis information regarding a contaminated package sample may comprise detail information of a contamination classification scheme. As illustrated in FIG. 3b, in such embodiments, the generation of the table 300 (as will be described in more detail below in connection with action 407) comprises the detail information of the contamination classification scheme 313, as described above in connection with the laboratory 130 and the analysis system 132. It is to be noted that the concept of "contaminated" is to be interpreted broadly and include any classification in terms of compliance or non-compliance with specifications regarding package integrity etc. as discussed above.

Action 405

The sampling records 201 and the analysis information are processed. This processing generates information that links contaminated package samples with sampling occasions.

For example, in some embodiments the analysis information regarding a contaminated package sample comprises information that represents a point in time at which the package sample was filled in the filling machine. In these embodiments, the processing of the sampling records 201 and the analysis information comprises a comparison between the information that represents a point in time at which the package sample was filled (e.g. a timestamp or a serial number obtained from the sample) and any of the first time stamp and the second time stamp. In this way, any contaminated sample is linked to the sampling occasion when the sample was taken, making it possible to generate a complete table (as will be described below) comprising sampling occasions, production times, sampling times, number of samples taken, number of samples without defects, number of samples contaminated (or with other defects as discussed above).

Action 407

As illustrated in FIG. 3a, a table 300 is generated that comprises, for each sampling occasion, the first time stamp for the sampling occasion 303, the information that describes a trigger for the sampling occasion 305, the number of package samples taken at the sampling occasion 307, the second time stamp that specifies when the package samples were taken 309 and a number of contaminated package samples at the sampling occasion 311.

For example, the table that is generated may be stored in the database 149. Subsequent tools (not part of the present disclosure) may then operate on this database 149 to produce simple, easy to read quality reports, related to specific indicators that simplifies and improves efficiency of service and support processes. Full detailed data can be downloaded from the database 149 and used by people with specific competence to produce sophisticated statistical analysis.

Action 420

In some embodiments, in addition to obtaining information from the filling machine 110, auxiliary information regarding a contaminated package may be obtained where this auxiliary information comprises information that represents a point in time at which the contaminated package was filled in the filling machine 110. In such embodiments, the sampling records and the auxiliary information is processed, whereby information is obtained that links the contaminated package with the point in time at which it was filled, and the generation of the table comprises the information that links the contaminated package with the point in time at which it was filled 315, as is illustrated in FIG. 3c. For example, information that represents a point in time at which the package sample was filled may be a timestamp, a serial number etc., obtained from the package.

As FIG. 1 illustrates the auxiliary information regarding a contaminated package may be obtained from a location at which packages filled by the filling machine are stored, for example the warehouse 120 or the retailer 150. In a case where the auxiliary information is obtained from the warehouse 120, detection of a contaminated package is performed by the warehouse operator 129 and provided via the PLMS-W 124 to the PLMS-C 146. However, a case where five auxiliary information is obtained from the retailer 150, detection of a contaminated package is performed by the retailer operator 159 and provided via the report 155, e.g. via any suitable electronic communication means that can provide, for the PLMS-C 146, readable data.

Figure 5:
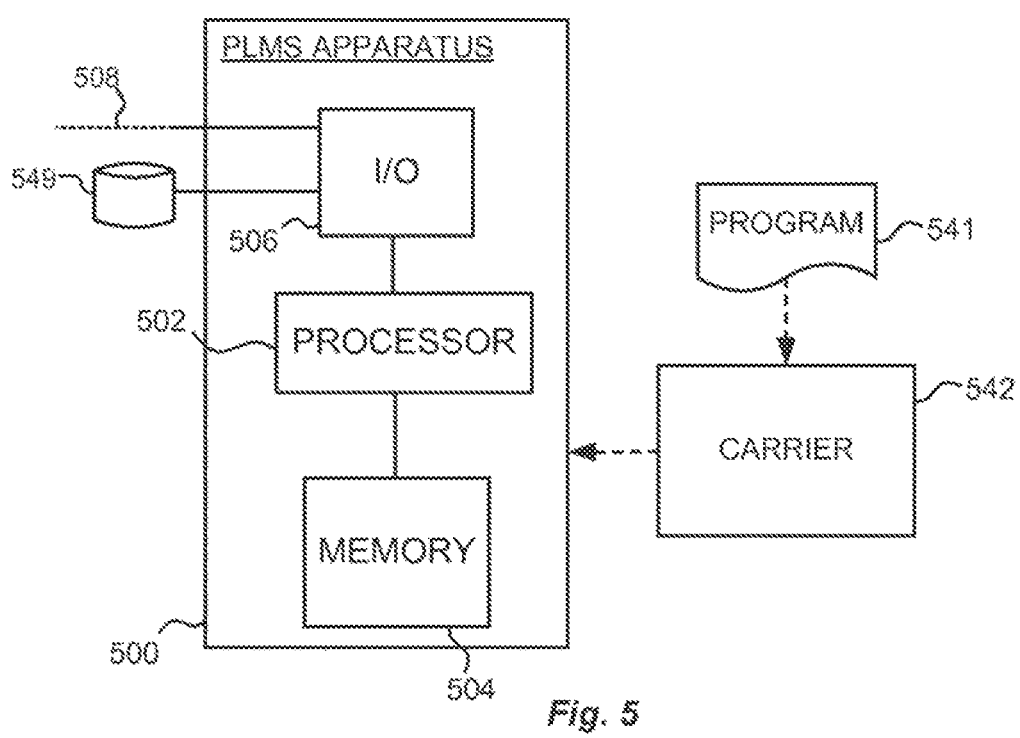
FIG. 5 is a block diagram that schematically illustrates a packaging line monitoring system apparatus.

FIG. 5 illustrates schematically a packaging line monitoring system apparatus 500, e.g. corresponding to the PLMS-C 146 in FIG. 1. The packaging line monitoring system apparatus comprises a processor 502, a memory and input/output circuitry 506. The input/output circuitry 506 may be connected to a database 549, such as the database 149 in FIG. 1, and also connected to any other apparatus via a connection 508. As the skilled person will realize the connection 508 may simply be a connection to a digital network that is suitably adapted to interconnect the packaging line monitoring system apparatus 500 with the PLMS-FM 110, the PLMS-W 124 and the PLMS-LAB 134 in FIG. 1.

The memory 504 contains instructions executable by the processor 502 whereby the processor 502 is operative to control the packaging line monitoring system apparatus 500 by:

obtaining 401, from a package filling machine 110, information regarding sampling occasions in the form of a plurality of sampling records 201, each sampling record comprising a first time stamp 203 for the sampling occasion, information that describes a trigger 205 for the sampling occasion, a number of package samples 207 taken at the sampling occasion, and a second time stamp 209 that specifies when the package samples were taken, obtaining 403, from a package sample analysis system 132,117, analysis information regarding contaminated package samples 133, processing 408 the sampling records and the analysis information, whereby information is obtained that links contaminated package samples with sampling occasions, and generating 407 a table 300 comprising, for each sampling occasion, the first time stamp for the sampling occasion 303, the information that describes a trigger for the sampling occasion 305, the number of package samples taken at the sampling occasion 307, the second time stamp that specifies when the package samples were taken 309, and a number of contaminated package samples 311 at the sampling occasion.

In some embodiments, the memory 504 contains instructions executable by the processor 502 whereby the processor 502 is operative to control the packaging line monitoring system apparatus 500 such that:

the analysis information regarding a contaminated package sample composes information that represents a point in time at which the package sample was filled in the filling machine, such as any of a time stamp and a serial number, and such that the processing of the sampling records and the analysis information comprises a comparison between the information that represents a point in time at which the package sample was filled and any of the first time stamp and the second time stamp.

In some embodiments, the memory 504 contains instructions executable by the processor 502 whereby the processor 502 is operative to control the packaging line monitoring system apparatus 500 such that the information that describes a trigger for the sampling occasion comprises information about an event in the package filling machine. For example, the event in the package filling machine may be any of production start, re-start after short or normal stop, longitudinal sealing strip splice, packaging material reel splice, change of filling product, change of filling tank, and end of production.

In some embodiments, the memory 504 contains instructions executable by the processor 502 whereby the processor 502 is operative to control the packaging line monitoring system apparatus 800 such that the information that describes a trigger for the sampling occasion comprises information that specifies that the sampling occasion has been chosen randomly or pseudo-randomly.

In some embodiments, the memory 504 contains instructions executable by the processor 502 whereby the processor 502 is operative to control the packaging line monitoring system apparatus 500 such that the analysis information regarding a contaminated package sample comprises detail information 313 of a contamination classification scheme, and such that the generation of a table comprises the detail information of the contamination classification scheme.

In some embodiments, the memory 504 contains instructions executable by the processor 502 whereby the processor 502 is operative to control the packaging line monitoring system apparatus 500 such that the obtaining of analysis information comprises obtaining the analysis information from a laboratory 130.

In some embodiments, the memory 504 contains instructions executable by the processor 502 whereby the processor 502 is operative to control the packaging line monitoring system apparatus 500 such that the obtaining of analysis information comprises obtaining the analysis information from the filling machine 110.

In some embodiments, the memory 504 contains instructions executable by the processor 502 whereby the processor 502 is operative to control the packaging line monitoring system apparatus 500 by:

obtaining 420 auxiliary information 315 regarding a contaminated package 123, 153, where the auxiliary information comprises information that represents a point in time at which the contaminated package was filled in filling machine, processing 421 the sampling records and the auxiliary information, whereby information is obtained that links the contaminated package with the point in time at which it was filled, and by;

the generation of the table comprises the information that links the contaminated package with the point in time at which it was filled.

In some embodiments, the memory 504 contains instructions executable by the processor 502 whereby the processor 502 is operative to control the packaging line monitoring system apparatus 500 such that the auxiliary information regarding a contaminated package is obtained from a location at which packages filled by the filling machine are stored, said location being a warehouse 120 or a retailer 150.

The instructions that are executable by the processor 502 may be software in the form of a computer program 541. The computer program 541 may be contained in or by a carrier 542, which may provide the computer program 541 to the memory 504 and processor 502. The carrier 542 may be in any suitable form including an electronic signal, an optical signal, a radio signal or a computer readable storage medium.

The invention claimed is:

1. A method in a packaging line monitoring system, the method comprising:

obtaining, from a package filling machine, information regarding sampling occasions in the form of a plurality of sampling records, each sampling record comprising a first time stamp for the sampling occasion, information that describes a trigger for the sampling occasion, a number of package samples taken at the sampling occasion, and a second time stamp that specifies when the package samples were taken, obtaining, from a package sample analysis system, analysis information regarding contaminated package samples, processing the sampling records and the analysis information, whereby information is obtained that links contaminated package samples with sampling occasions, generating a table comprising, for each sampling occasion, the first time stamp for the sampling occasion, the information that describes a trigger for the sampling occasion, the number of package samples taken at the sampling occasion, the second time stamp that specifies when the package samples were taken, and a number of contaminated package samples at the sampling occasion, obtaining auxiliary information regarding a contaminated package, where the auxiliary information comprises information that represents a point in time at which the contaminated package was filled in the filling machine, processing the sampling records and the auxiliary information, whereby information is obtained that links the contaminated package with the point in time at which it was filled, the generation of the table comprising the information that links the contaminated package with the point in time at which it was filled, the obtaining of the analysis information comprising obtaining the analysis information from the filling machine, the auxiliary information regarding the contaminated package being obtained from a location at which packages filled by the filling machine are stored and wherein said location is a warehouse, or the auxiliary information regarding the contaminated package being obtained from a location at which packages filled by the filling machine are stored and wherein said location is a retailer, the analysis information regarding a contaminated package sample comprising information that represents a point in time at which the package sample was filled in the filling machine, the processing of the sampling records and the analysis information comprises a comparison between the information that represents a point in time at which the package sample was filled and any of the first time stamp and the second time stamp, the information that represents the point in time at which the package sample was filled comprises any of a time stamp and a serial number, the analysis information regarding a contaminated package sample comprises detail information of a contamination classification scheme, and the generation of a table comprises the detail information of the contamination classification scheme.

2. The method of claim 1, wherein the information that describes a trigger for the sampling occasion comprises information about an event in the package filling machine.

3. The method of claim 2, wherein the event in the package filling machine is any of:
production start,
re-start after short or normal stop,
longitudinal sealing strip splice,
packaging material reel splice,
change of filling product,
change of filling tank, and
end of production.

4. The method of claim 1, wherein the information that describes a trigger for the sampling occasion comprises information that specifies that the sampling occasion has been chosen randomly or pseudo-randomly.

5. The method of claim 1, wherein the obtaining of analysis information comprises obtaining the analysis information from a laboratory.

6. A computer program, comprising instructions which, when executed on at least one processor in a packaging line monitoring system apparatus, cause the packaging line monitoring system apparatus to carry out the method according to claim 1.

7. A carrier comprising the computer program of claim 6, wherein the carrier is one of an electronic signal, an optical signal, a radio signal and a computer readable storage medium.

8. A packaging line monitoring system apparatus, comprising a processor, a memory and input/output circuitry, said memory containing instructions executable by said processor whereby said processor is operative to control the packaging line monitoring system apparatus by:

obtaining, from a package filling machine, information regarding sampling occasions in the form of a plurality of sampling records, each sampling record comprising a first time stamp for the sampling occasion, information that describes a trigger for the sampling occasion, a number of package samples taken at the sampling occasion, and a second time stamp that specifies when the package samples were taken, obtaining, from a package sample analysis system, analysis information regarding contaminated package samples, processing the sampling records and the analysis information, whereby information is obtained that links contaminated package samples with sampling occasions, and generating a table comprising, for each sampling occasion, the first time stamp for the sampling occasion, the information that describes a trigger for the sampling occasion, the number of package samples taken at the sampling occasion, the second time stamp that specifies when the package samples were taken, and a number of contaminated package samples at the sampling occasion obtaining auxiliary information regarding a contaminated package, where the auxiliary information comprises information that represents a point in time at which the contaminated package was filled in the filling machine, processing the sampling records and the auxiliary information, whereby information is obtained that links the contaminated package with the point in time at which it was filled, the generation of the table comprising the information that links the contaminated package with the point in time at which it was filled, the obtaining of the analysis information comprising obtaining the analysis information from the filling machine, the auxiliary information regarding the contaminated package being obtained from a location at which packages filled by the filling machine are stored and wherein said location is a warehouse, or the auxiliary information regarding the contaminated package being obtained from a location at which packages filled by the filling machine are stored and wherein said location is a retailer, the analysis information regarding a contaminated package sample comprising information that represents a point in time at which the package sample was filled in the filling machine, the processing of the sampling records and the analysis information comprises a comparison between the information that represents a point in time at which the package sample was filled and any of the first time stamp and the second time stamp, the information that represents the point in time at which the package sample was filled comprises any of a time stamp and a serial number, the analysis information regarding a contaminated package sample comprises detail information of a contamination classification scheme, and the generation of a table comprises the detail information of the contamination classification scheme.

* * * * *